US010539667B2

(12) United States Patent
Peng et al.

(10) Patent No.: US 10,539,667 B2
(45) Date of Patent: Jan. 21, 2020

(54) HIGH POWER, HIGH FREQUENCY PULSER FOR USE IN ULTRASOUND

(71) Applicant: General Electric Company, Schenectady, NY (US)

(72) Inventors: Han Peng, Niskayuna, NY (US); Juan Antonio Sabate, Niskayuna, NY (US); Kieran Andrew Wall, Moss (NO)

(73) Assignee: General Electric Company, Schenectady, NY (US)

( * ) Notice: Subject to any disclaimer, the term of this patent is extended or adjusted under 35 U.S.C. 154(b) by 476 days.

(21) Appl. No.: 15/400,807

(22) Filed: Jan. 6, 2017

(65) Prior Publication Data

US 2018/0196129 A1 Jul. 12, 2018

(51) Int. Cl.
*A61B 8/00* (2006.01)
*G01S 7/52* (2006.01)

(52) U.S. Cl.
CPC ........ *G01S 7/5202* (2013.01); *G01S 7/52085* (2013.01); *A61B 8/4483* (2013.01)

(58) Field of Classification Search
None
See application file for complete search history.

(56) References Cited

U.S. PATENT DOCUMENTS

| 7,332,749 | B2 | 2/2008 | Shimizu et al. |
| 8,786,342 | B1 | 7/2014 | Achiriloaie et al. |
| 9,238,808 | B2 | 1/2016 | Caiafa et al. |
| 2015/0160285 | A1 | 6/2015 | Joh et al. |
| 2016/0197215 | A1 | 7/2016 | Kozyrev et al. |
| 2017/0326588 | A1* | 11/2017 | Broad .................. A61B 8/4444 |

FOREIGN PATENT DOCUMENTS

CN 204481779 U 7/2015

OTHER PUBLICATIONS

Wang, H., et al.; "A GaN pulse width modulation integrated circuit", Power Semiconductor Devices & IC's (ISPSD), 2014 IEEE 26th International Symposium on, pp. 430-433, Jun. 15-19, 2014, Waikoloa, HI.
Boni, E., et al.; "High frequency GaN-based pulse generator with active T/R switch circuit", Ultrasonics Symposium (IUS), 2014 IEEE International, pp. 1595-1598, Sep. 3-6, 2014, Chicago, IL.
Wang, H., et al.; "A GaN Pulse Width Modulation Integrated Circuit for GaN Power Converters", IEEE Transactions on Electron Devices, vol. 62, Issue: 4, pp. 1143-1149, Apr. 2015.

* cited by examiner

*Primary Examiner* — Kennedy Schaetzle

(57) ABSTRACT

An ultrasound pulse generator circuit includes a first gate driver electrically coupled to a first gallium nitride (GaN) transistor, a second gate driver electrically coupled to a second GaN transistor, a first snubber circuit, a second snubber circuit, and a transformer. The first snubber circuit and the second snubber circuit each include a respective capacitor and resistor and each snubber circuit is configured to clamp a voltage overshoot when present. Further, the transformer generates an output signal when operated and the third transformer is electrically connected downstream of the first GaN transistor, the second GaN transistor, the first snubber circuit, and the second snubber circuit. In addition, the transformer includes multiple windings.

20 Claims, 15 Drawing Sheets

HIGH POWER, HIGH FREQUENCY PULSER FOR USE IN ULTRASOUND

This invention was made with Government support under contract number NNC09BA02B with a Sub contract number SPACEDOC 2013-003 awarded by National Aeronautics and Space Administration. The Government has certain rights in the invention.

BACKGROUND

Medical diagnostic ultrasound is an imaging modality that employs ultrasound waves to probe the acoustic properties of the body of a patient and produce a corresponding image. Generation of sound wave pulses and detection of returning echoes is typically accomplished via a plurality of transducers located in the probe. Such transducers typically include electromechanical elements capable of converting electrical energy into mechanical energy for transmission and mechanical energy back into electrical energy for receiving purposes. Some ultrasound probes include up to thousands of transducers arranged as linear arrays.

In conventional ultrasound systems, a silicon pulse generator may be employed as part of the transducer driving mechanism, e.g., as part of the ultrasound pulsing circuits. However, certain applications, such as ultrasound surgery, shear wave, drug delivery, and so forth, require high energy delivering ultrasound pulsing circuits with ultra-long burst mode pulse length, multi-MHz pulse frequencies, and high pulse amplitude, which silicon-based circuitry may be unsuitable for delivering.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, an ultrasound system includes a transmitter beam former configured to send a signal. In addition, the system includes a first gate driver electrically coupled to a first GaN transistor and the first gate driver is configured to receive the signal from the transmitter beam former. Further, the system includes a second gate driver electrically coupled to a second GaN transistor and the second gate driver is configured to receive the signal from the transmitter beam former. The system also includes a first snubber circuit and a second snubber circuit, and each snubber circuit includes a respective capacitor and resistor, and each snubber circuit is configured to clamp a voltage overshoot when present. In addition, the system includes a transformer configured to generate an output signal when operated. The transformer is electrically connected downstream of the first GaN transistor, the second GaN transistor, the first snubber circuit, and the second snubber circuit. Furthermore, the transformer includes a plurality of windings in a center tapped configuration. The system also includes a transmit/receive switch configured to receive the output signal. Lastly, the system includes a transducer array electrically coupled to the transmit/receive switch, and the transducer array generates ultrasound pulses in response to the output signal.

In another embodiment, a method includes receiving a signal at a first gate driver and a second gate driver. The method further includes transforming the signal from the first gate driver into a first pulsed signal with a first GaN transistor, and transforming the signal from the second gate driver into a second pulsed signal with a second GaN transistor. In addition, the method includes passing the first pulsed signal through a first snubber circuit, and the first snubber circuit includes a first resistor and a first capacitor. The method also includes passing the second pulsed signal through a second snubber circuit, and the second snubber circuit includes a second resistor and a second capacitor. Moreover, the method includes passing the first pulsed signal and the second pulsed signal through a transformer. The transformer includes multiple windings in a center tapped configuration, and the first pulsed signal and the second pulsed signal become a single output signal after passing through secondary winding of the transformer.

In a further embodiment, an ultrasound pulse generator circuit includes electronic circuitry configured to receive a signal from a beam former circuit and generate an output suitable for driving an ultrasound transducer array. The electronic circuitry includes one or more GaN transistors.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

In conventional ultrasound imaging systems, a silicon pulse generator may be employed as part of the ultrasound pulsing circuits. However, certain applications require high power ultrasound pulsing circuits capable of tens of millisecond burst mode pulse length with multi-MHz pulse frequency, and silicon circuitry may be unsuitable. In accordance with the present approach, to address these instances, a high power gallium nitride (GaN) transistor based pulse generator is employed instead to provide a high energy delivery ultrasound pulsing circuit.

Figure 1:
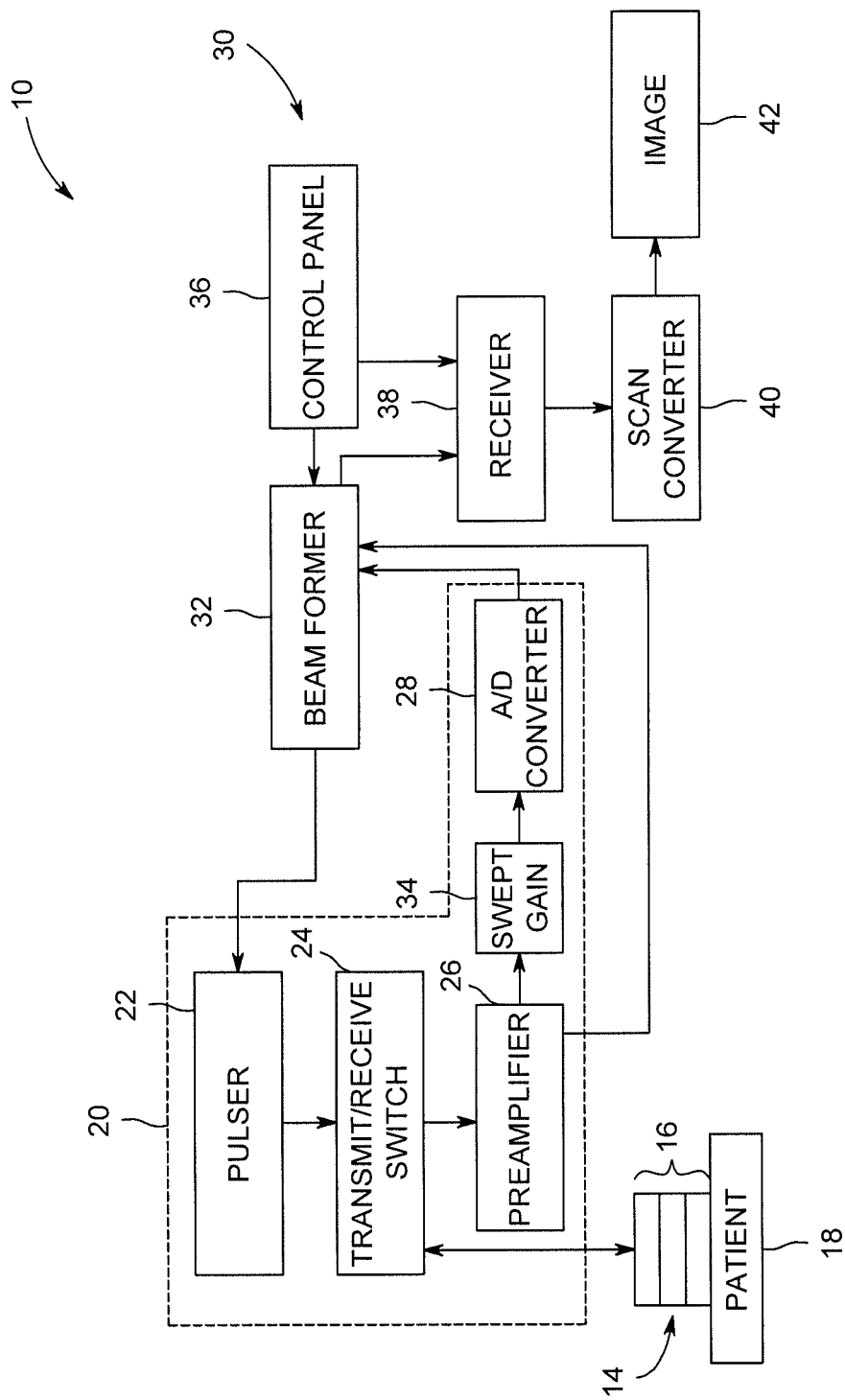
FIG. 1 is an embodiment of a block diagram of an ultrasound system, in accordance with aspects of the present disclosure.

Turning now to the drawings, FIG. 1 is a block diagram illustrating an embodiment of an ultrasound system 10, such as an ultrasound system in which the presently disclosed GaN pulse circuitry may be employed. In the depicted embodiment, the ultrasound system 10 is a digital acquisition and beam former system, but in other embodiments, the ultrasound system 10 may be any suitable type of ultrasound system, not limited to the type or structures depicted here. The illustrated ultrasound system 10 includes a transducer array 14 having transducer elements 16 suitable for contact with a subject or patient 18 during an imaging procedure. As will be appreciated by those skilled in the art, transducer elements 16 may be fabricated from materials, such as, but not limited to lead zirconate titanate (PZT), polyvinylidene difluoride (PVDF) and composite PZT. It should be noted that the transducer array 14 is configured as a two-way transducer and capable of transmitting ultrasound waves into and receiving such energy from the subject or patient 18. In transmission mode, the transducer array elements 16 convert the electrical energy into ultrasound waves and transmit it into the patient 18. In reception mode, the transducer array elements 16 convert the ultrasound energy received from the patient 18 (backscattered waves) into electrical signals.

Each transducer element 16 is associated with respective transducer circuitry 20. That is, in the illustrated embodiment, each transducer element 16 in the array 14 has a pulser 22, a transmit/receive switch 24, a preamplifier 26, a swept gain 34, and an analog to digital (A/D) converter 28. For example, in an embodiment in which the transducer array 14 includes 128 transducer elements 16, there would be 128 sets of transducer circuitry 20, one for each transducer element 16. In other implementations, this arrangement may be simplified or otherwise changed, components shown in the circuitry 20 may be provided upstream or downstream of the depicted arrangement; however, the basic functionality depicted will typically still be provided for each transducer element 16.

Further, a variety of other imaging components 30 are provided to enable image formation with the ultrasound system 10. Specifically, the depicted example of an ultrasound system 10 also includes a beam former 32, a control panel 36, a receiver 38, and a scan converter 40 that cooperate with the transducer circuitry 20 to produce an image 42. For example, in one embodiment, during operation of the ultrasound system 10, the image 42 is created using a pulse echo method of ultrasound production and detection. In this embodiment, a pulse is directionally transmitted into the patient 18 via the transducer array 14 and then is partially reflected from tissue interfaces that create echoes that are detected by the transducer elements 16.

More specifically, the pulser 22, which is capable of operating as a transmitter, provides an electrical voltage suitable for excitation of the transducer elements 16 and may adjust the applied voltage to control the output transmit power. The transmit/receive switch 24 is synchronized with the pulser 22 and is capable of isolating the high voltage used for pulsing from the amplification stages during receiving cycles. The swept gain 34 reduces the dynamic range of the received signals prior to digitization. The beam former 32 is capable of providing digital focusing, steering, and summation of the beam, and the receiver 38 processes the received data for display to an operator. For example, in one embodiment, the beam former 32 may control application-specific integrated circuits (ASICs) including the transmit/receive switch 24, the A/D converter 28, the preamplifier 26, and so forth, for each of the transducer elements 16. In this way, the beam former 32 may control and generate electronic delays in the transducer array 14 to achieve the desired transmit and receive focusing, as specified by the ultrasound operational parameters input via the control panel 36. Further, the scan converter 40 receives the processed data from the receiver 38 and produces the image 42, which may be displayed to an operator, for example, on an associated monitor.

Figure 2:
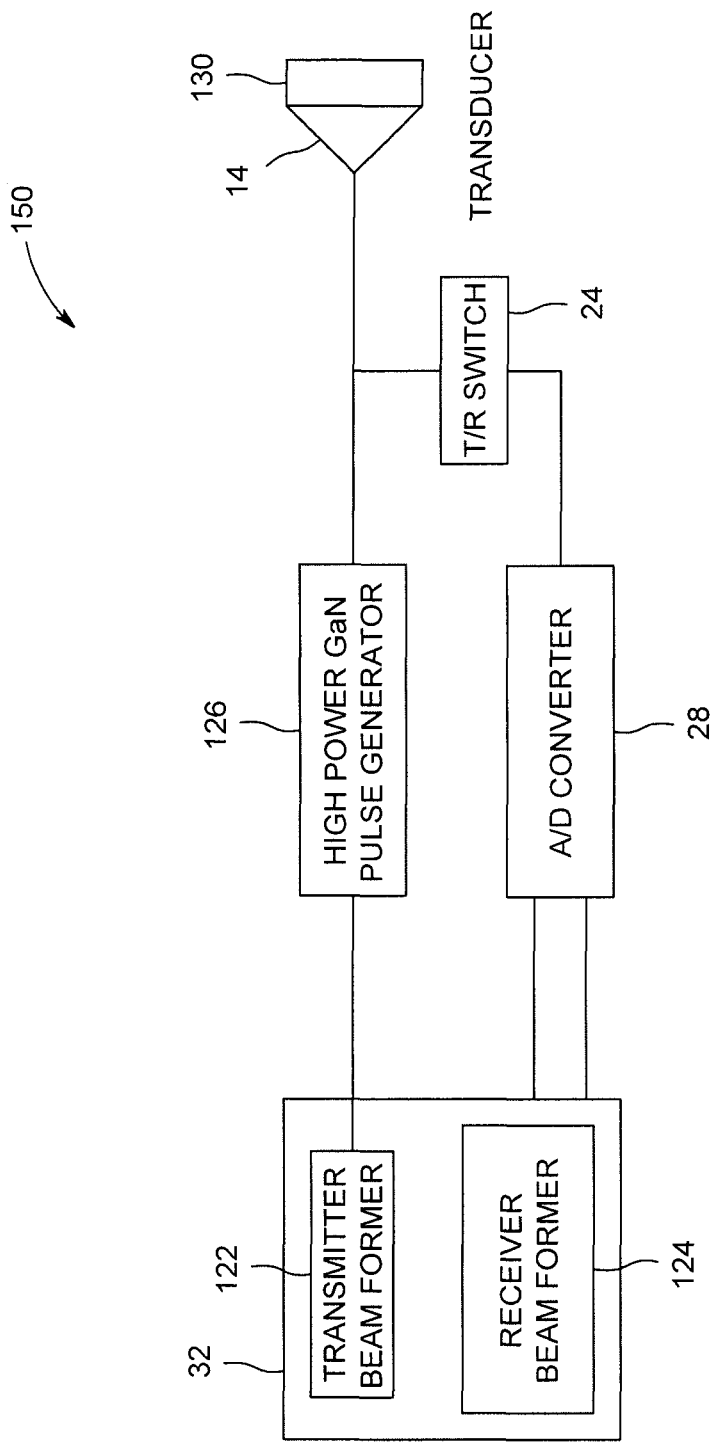
FIG. 2 is an embodiment of an ultrasound control module using a gallium nitride (GaN) pulse generator, in accordance with aspects of the present disclosure.

In accordance with the present approach, FIG. 2 depicts a schematic depiction of certain components of the system of FIG. 1 relevant to discussion of an embodiment of an ultrasound control module using a GaN pulse generator. The illustrated ultrasound system 150 includes example components connected in a manner suitable for data acquisition and processing. However, the illustrated embodiment is merely an example and is not meant to limit the forms, components, or data flow encompassed by presently disclosed embodiments. Indeed, in other embodiments, the architecture of system 150 may include a variety of hardware and software components. For example, the system may include hardware components, such as circuit boards with digital signal processors. Also, the system 150 may incorporate various processor-executable instructions or routines stored on a variety of media, storage devices, or hardware which may be included in the system 150.

In the illustrated embodiment, the transducer array 14 is provided with a front face or acoustic lens structure 130 that is adapted to contact the subject 18, such that an ultrasonic scan may be performed to analyze internal features of the subject 18. As noted above, the same transducer elements both generate and receive ultrasound energy in a pulse-echo mode, although different elements on the transducer may be used for these functions in some embodiments.

A beam former control unit 32 contains both a transmitter beam former 122 and a receiver beam former 124. The transducer array 14 is connected via transmitter/receiver switching circuitry 24 to the transmitter beam former 122 and the receiver beam former 124. The transmitter/receiver switching circuitry 24 switches the electrical connections between the transducer array 14 and the transmitter beam former 122 and the receiver beam former 124. In operation, the transmitter beam former 122 is connected to the transducer array 14 when ultrasound energy has to be transmitted into the body of the subject 18, and the receiver beam former 124 is connected to the transducer array 14 when the transducer array 14 receives the echo signals from the tissue layers of the subject 18.

That is, the illustrated transducer array 14 includes a two-way transducer. In order to transmit ultrasound waves into the subject 18, in the depicted example, the transmitter beam former 122 sends a signal to the depicted high power GaN pulse generator 126. As discussed herein, the pulse generator circuit, relative to convention pulse generation circuits is a high-frequency, high power density pulser circuit that is capable of generating and sustaining a pulsing frequency of 10 MHz with a pulse duration of greater than 40 ms such as 50 ms or more and a 3 second repetition rate (at a ±90 V pulse amplitude and an output current up to 1.5 A). In operation, the GaN pulse generator circuitry discussed herein will, in certain embodiments, receive a signal from the transmitter beam former 122 and transform the signal into a high-energy, pulsed signal which can then be provided to the transducer array 14 to drive the array to generate responsive ultrasonic pulses. The transducer array 14 then sends the pulsed ultrasound waves through the acoustic lens structure 130 and into the subject 18. When ultrasound waves are transmitted into the subject 18, the ultrasound waves are backscattered off the tissue and blood within the subject 18. The transducer elements of the transducer array 14 receive the backscattered waves at different times, depending on the distance into the tissue they return from, and the angle with respect to the surface of the transducer array 14 at which they return. The transducer elements are responsive to the backscattered waves and convert the ultrasound energy from the backscattered waves into electrical signals.

The electrical signals received by the transducer array 14 are routed through the transmitter/receiver switching circuitry 24 to the receiver beam former 124. The receiver beam former 124 amplifies the received signals after proper gain compensation, and an analog-to-digital converter (ADC) 28 converts these received analog signals from each transducer array element to digitized signals sampled uniformly in time, which are stored temporarily in system memory. However, as depicted in FIG. 1, it may be beneficial to include the preamplifier 26 and the swept gain 34. The digitized signals correspond to the backscattered waves received by each transducer element at various times. After digitization, the signals still preserve the amplitude and phase information of the backscattered waves.

Figure 3:
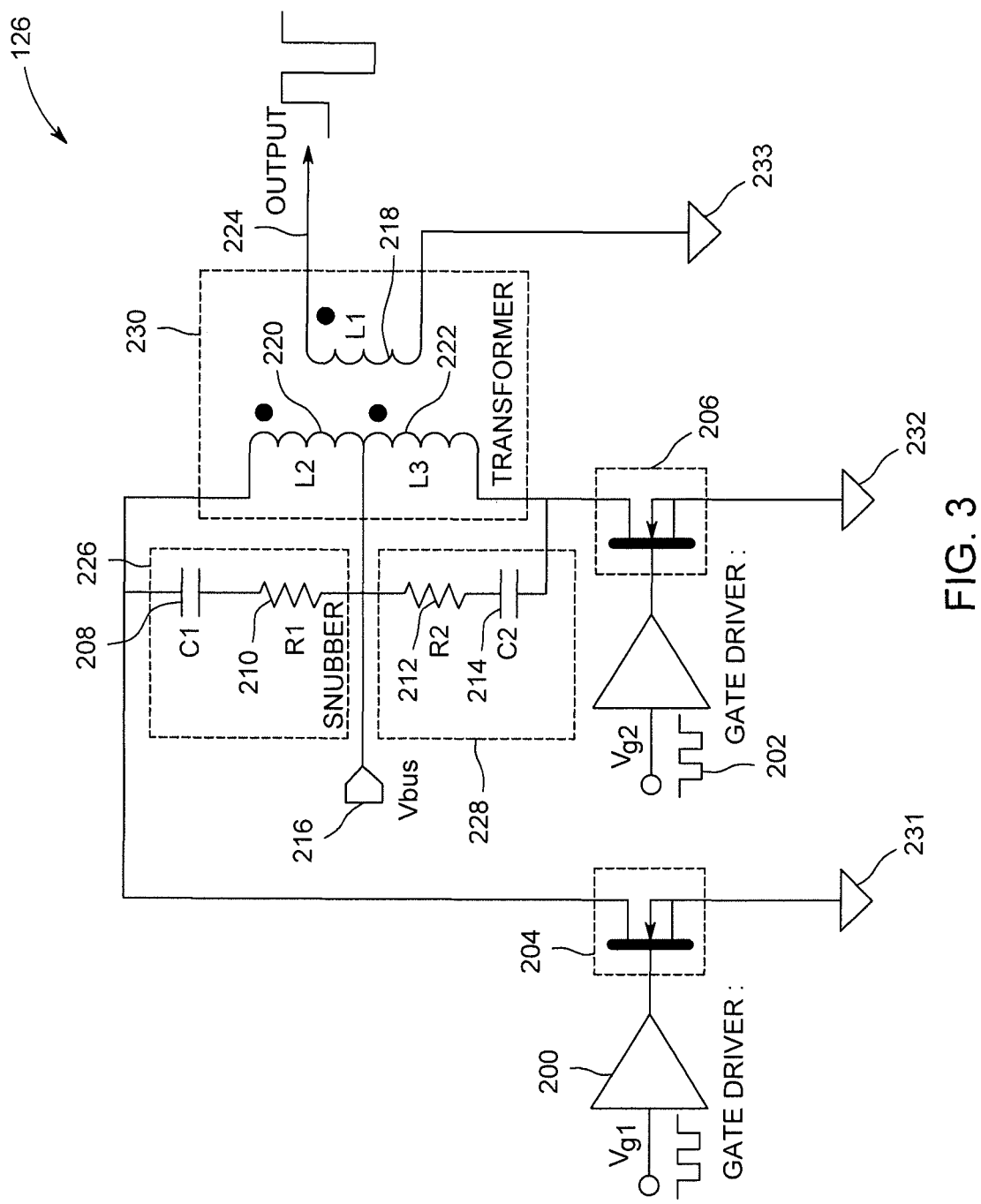
FIG. 3 is a diagram of an embodiment of a GaN pulse generator, in accordance with aspects of the present disclosure.

FIG. 3 includes an embodiment of a GaN pulse generator circuit as discussed herein. The depicted example is in the form of transformer push-pull pulser circuit. With respect to this embodiment, and as shown in the circuit flow described below, a signal from a transmit beam former is received at split gates and the two split signals are, subsequently, separately transformed using the GaN transistor devices shown into separate pulsed signals. These pulsed signals are joined downstream (after being passed through respective snubber circuits to suppress voltage transients) before being combined into an output signal that can be used to drive a downstream transducer array.

With this in mind, and by way of example, FIG. 3 depicts corresponding circuitry to implement pulse generation. In this circuit example, a first gate driver 200 is electrically coupled to a first power switch 204. The present embodiment also includes a second gate driver 202 electrically coupled to a second power switch 206. The first gate driver 200 and the second gate driver 202 receive a signal from the transmitter beam former 122. In accordance with the present approach, both the first power switch 204 and the second power switch 206 are a GaN high-electron-mobility transistor device. The benefits of using a GaN device instead of a silicon device are discussed below. The high power GaN pulse generator 126 also includes a high frequency, wide bandwidth transformer 230. In the present example, the transformer 230 is in a center tapped configuration. In a center tapped configuration, the secondary winding is divided into two windings, and each of the two windings may have the same voltage or different voltages.

A first passive snubber circuit 226 and a second passive snubber circuit 228 are connected between a power supply 216 and the first power switch 204 and the second power switch 206 respectively. In the depicted implementation, the first passive snubber circuit 226 includes a first capacitor 208 and a first resistor 210 and the second passive snubber circuit 228 includes a second capacitor 214 and a second resistor 214, although other snubber circuits may be utilized, such as including a diode, resistor, and capacitor. Both the first passive snubber circuit 226 and the second passive snubber circuit 228 clamp the voltage overshoot at the turn-off transition caused by transistor output capacitor, transformer leakage inductance, and the parasitic inductance in the loop. Both the first snubber circuit 226 and the second snubber circuit 228 can include alternative configurations. Also downstream of the first power switch 204 and the second power switch 206, in this embodiment, is a transformer 230 that includes a first winding 218, a second winding 220, and a third winding 222. The transformer 230 generates an output 224 which may drive a downstream transducer array. Also included in the high power GaN pulse generator 126 are a first signal ground 231, a second signal ground 232, and a third signal ground 233. The first signal ground 231 is coupled to the first power switch 204, the second signal ground 232 is coupled to the second power switch 206, and the third signal ground is coupled to the transformer 230. The first signal ground 231 and the second signal ground 232 may be the same signal ground. Further, the third signal ground 233 may be the same as or different from the first signal ground 231 and the second signal ground 232. It should be appreciated that although the present embodiment includes three signal grounds, more or less signal grounds may be included.

In one embodiment, the depicted circuit may be operated to generate a pulsed signal (i.e., output 224) for driving a downstream transducer array. In one such example, a pulse amplitude of 90 V is utilized. As will be appreciated, the pulse amplitude of the power supply 216 may vary based on the rating of the circuit and may be any suitable voltage, including 30 V, 50 V, 100 V, 200 V, 300 V, or more volts.

In an example where a bipolar output 224 is generated for driving transducers and the pulse amplitude is 90 V, the resulting output signal may be characterized as ±90 V. In such a bipolar arrangement, the power switches 204, 206 alternate between "on" and "off" positions such that there are two combined switch states (i.e., [Switch 1—On, Switch 2—Off] and [Switch 1—Off, Switch 2—On]). In such an example, the maximum peak of the pulse amplitude in a bipolar arrangement is one half of the device rating. For example, if the device is rated for 300 V, then the maximum peak of the pulse amplitude will be 150 V. In other implementations, the power switches may be operated in a tripolar arrangement, such as by adding a combined state in which both switches are off.

With respect to other operational parameters of the described circuit, in one implementation, the pulse frequency may be approximately 1 MHz up to approximately 10 MHz. In one example where the pulse amplitude of 90 V and the pulse frequency of 10 MHz are used, the pulse duration is 50 ms. As will be appreciated, the pulse duration may be longer or shorter depending on the application and will vary in response to the pulse amplitude and frequency. In a present example, the pulse repetition interval is 3 s. The pulse repetition interval is based, at least in part, on the pulse duration and the number of duty cycles.

Figure 4:
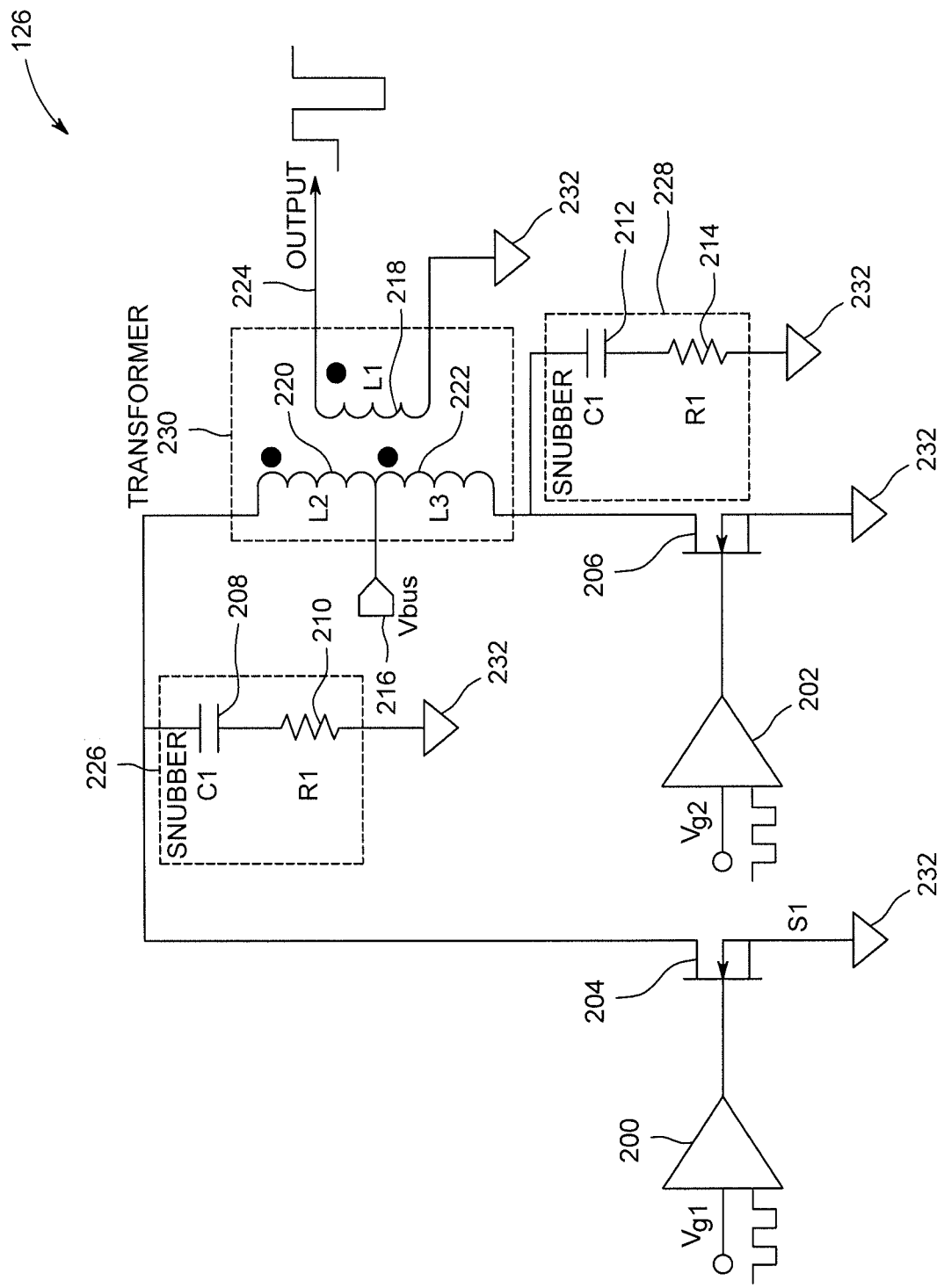
FIG. 4 is a diagram of an embodiment of a GaN pulse generator, in accordance with aspects of the present disclosure.

With the preceding in mind, FIG. 4 includes an alternative embodiment of a GaN pulse generator circuit, with the first passive snubber circuit 226 and the second passive snubber circuit 228 in an alternative configuration. In the depicted implementation, the first passive snubber circuit 226 is between the first power switch 204 and the signal ground 232. Further, the second passive snubber circuit 228 is between the second power switch 206 and the signal ground 232. As previously discussed, both the first power switch 204 and the second power switch 206 are a GaN high-electron-mobility transistor device. In the present embodiment, the transformer 230 is not downstream of either the first passive snubber circuit 226 or the second passive snubber circuit 228.

Figure 5:
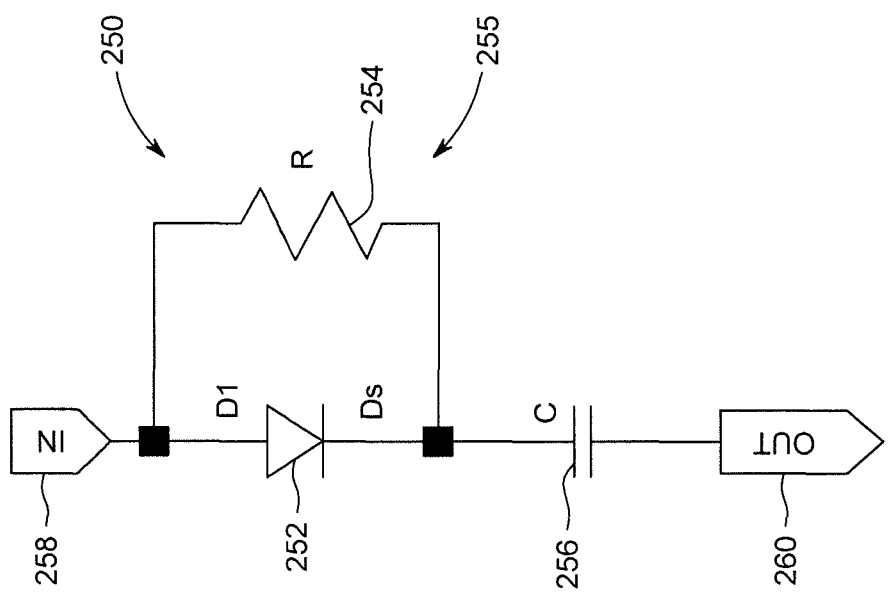
FIG. 5 is a diagram of an embodiment of a snubber circuit, in accordance with aspects of the present disclosure.

FIG. 5 includes an embodiment of an alternative configuration for a passive snubber circuit. A passive snubber circuit 250 receives an input 258 and generates an output 260. Downstream of the input 258, a diode 252 and a resistor 254 are electrically coupled in a parallel configuration and form a first section 255. Downstream of the first section 255 is a capacitor 256. Downstream of the capacitor 256 is the output 260.

Figure 6:
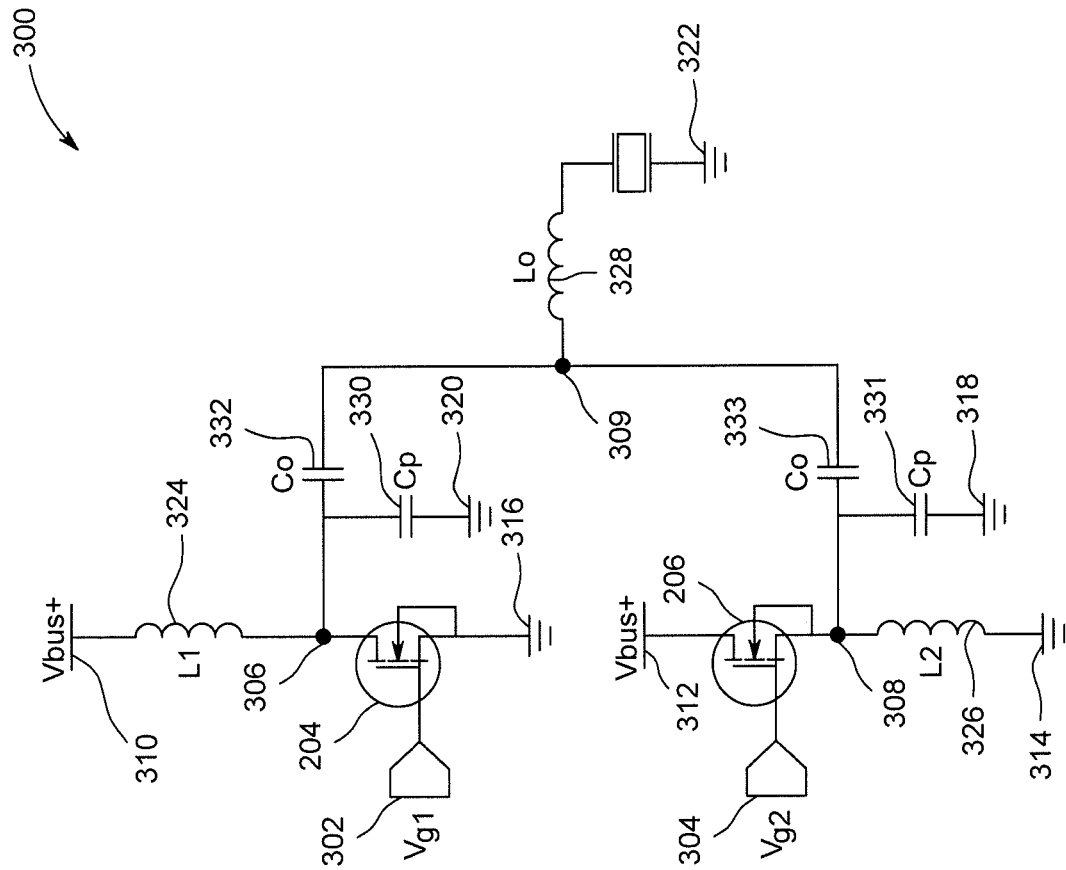
FIG. 6 is a diagram of an embodiment of a GaN pulse generator, in accordance with aspects of the present disclosure.

FIG. 6 includes an embodiment of a GaN pulse generator circuit as discussed herein. The depicted example is in the form of a class E power-amplifier pulser circuit. A first gate driver 302 is electrically coupled to the first power switch 204. The first power switch 204 is electrically coupled to a first ground 316. A first power supply 310 is upstream of a first winding 324. The first winding 324 and the first power switch 204 are electrically coupled at a junction 306. Downstream of the junction 306 is a first ground capacitor 330 and a fifth capacitor 332. Downstream of the first ground capacitor 330 is a second ground 320. Also included is a second gate driver 304 electrically coupled to the second power switch 206. As previously discussed, both the first power switch 204 and the second power switch 206 are a GaN high-electron-mobility transistor device. The second power switch 206 is downstream of a second power supply 312. In some embodiments, the first power supply 310 and the second power supply 312 may be the same power supply. A second winding 326 is coupled to the second power switch at a junction 308. A third ground 314 is electrically coupled to the second winding 326. Downstream of the junction 308 is a second ground capacitor 331 and a sixth capacitor 333. Downstream of the second ground capacitor 331 is a fourth ground 318. Downstream of the fifth capacitor 332 and the sixth capacitor 333 is a junction 309. Downstream of the junction 309 is a third winding 328 and a fifth ground 322.

Figure 7:
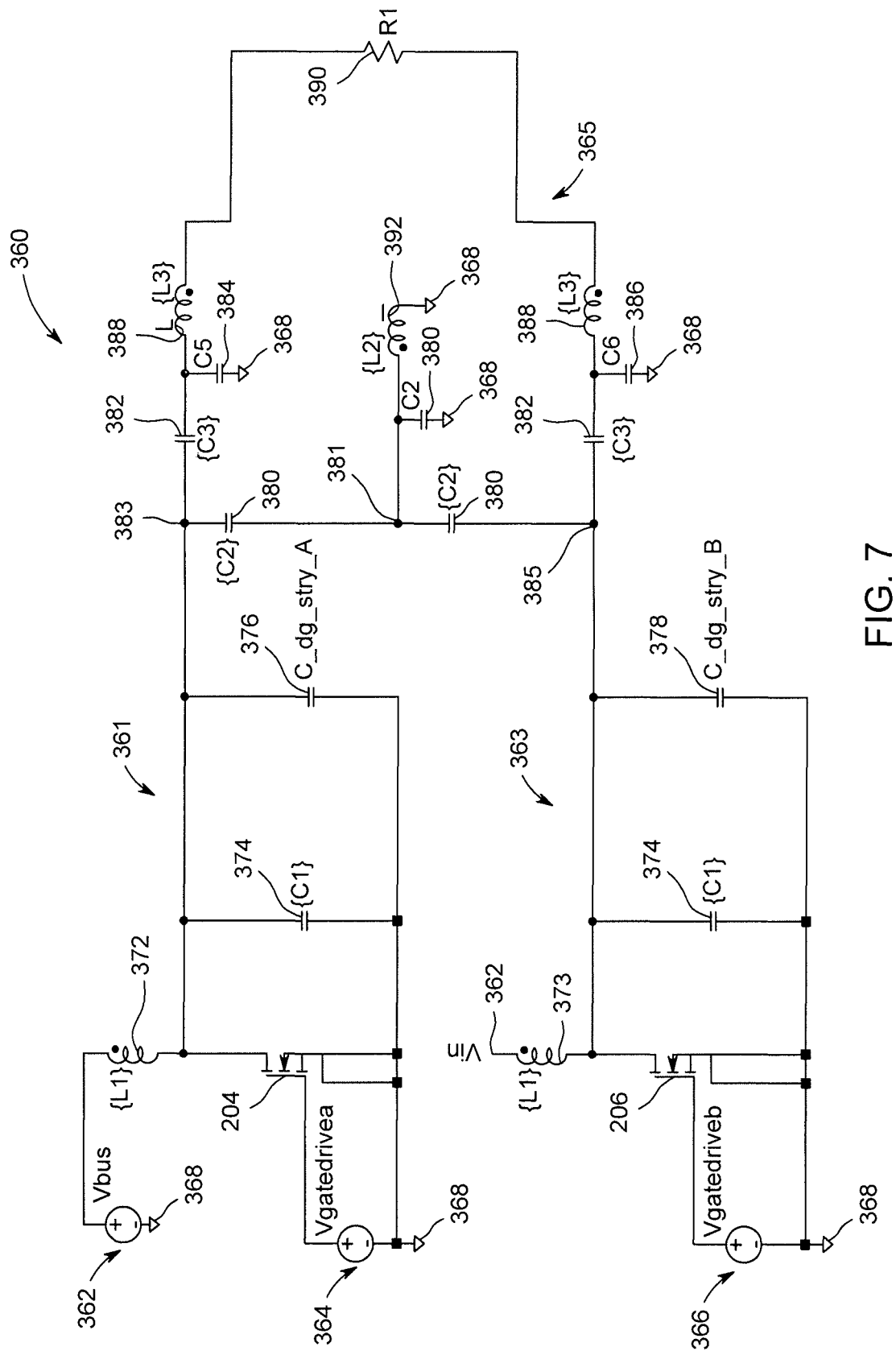
FIG. 7 is a diagram of an embodiment of a GaN pulse generator, in accordance with aspects of the present disclosure.

FIG. 7 includes a further embodiment of a GaN pulse generator circuit as discussed herein. The depicted example is in the form of a class EF2 push-pull pulser circuit. The GaN pulse generator circuit 360 includes a first section 361, a second section 363, and a third section 365 electrically coupled to one another. The first section 361 includes a power supply 362 electrically coupled to a winding 372. Downstream of the winding 372 is a parallel circuit including the first power switch 204 electrically coupled to a first gate driver 364, a C1 capacitor 374, and a capacitor 376. The first section 361 also includes grounds 368 coupled to the power supply 362 and the parallel circuit. The second section 363 is powered from same power supply 362 electrically coupled to a winding 373. Downstream of the winding 373 is a parallel circuit including the second power switch 206 electrically coupled to a second gate driver 366, the C1 capacitor 374, and a capacitor 378. The second section 363 includes ground 368 coupled to the power supply 362 and the parallel circuit. As previously discussed, both the first power switch 204 and the second power switch 206 are a GaN high-electron-mobility transistor device.

The first section 361 is electrically coupled to the third section 365 at a junction 383, and the second section 363 is electrically coupled to the third section 365 at a junction 385. The third section 365 includes a C2 capacitor 380 between the junction 383 and a junction 381, and another C2 capacitor 380 between the junction 385 and the junction 381. Downstream of the junction 381 is another C2 capacitor 380 and a winding 392. Both the C2 capacitor 380 and the winding 392 are coupled to grounds 368. The path between the junction 383 and the junction 385 includes a pair of C3 capacitors 382, a pair of L3 windings 388, an equivalent load resistor 390 representing the transducer load, a capacitor 384 coupled to the ground 368, and a capacitor 386 coupled to the ground 368. The circuits of FIGS. 6 and 7 are capable of being operated at the same pulse frequency as the circuit of FIG. 3 (i.e., 1 to 10 MHz). However, the pulse amplitude may be different than the 90 V used in the circuit of FIG. 3. Accordingly, the pulse duration, pulse repetition, and output pulses would also all be different from the circuit of FIG. 3.

Figure 8:
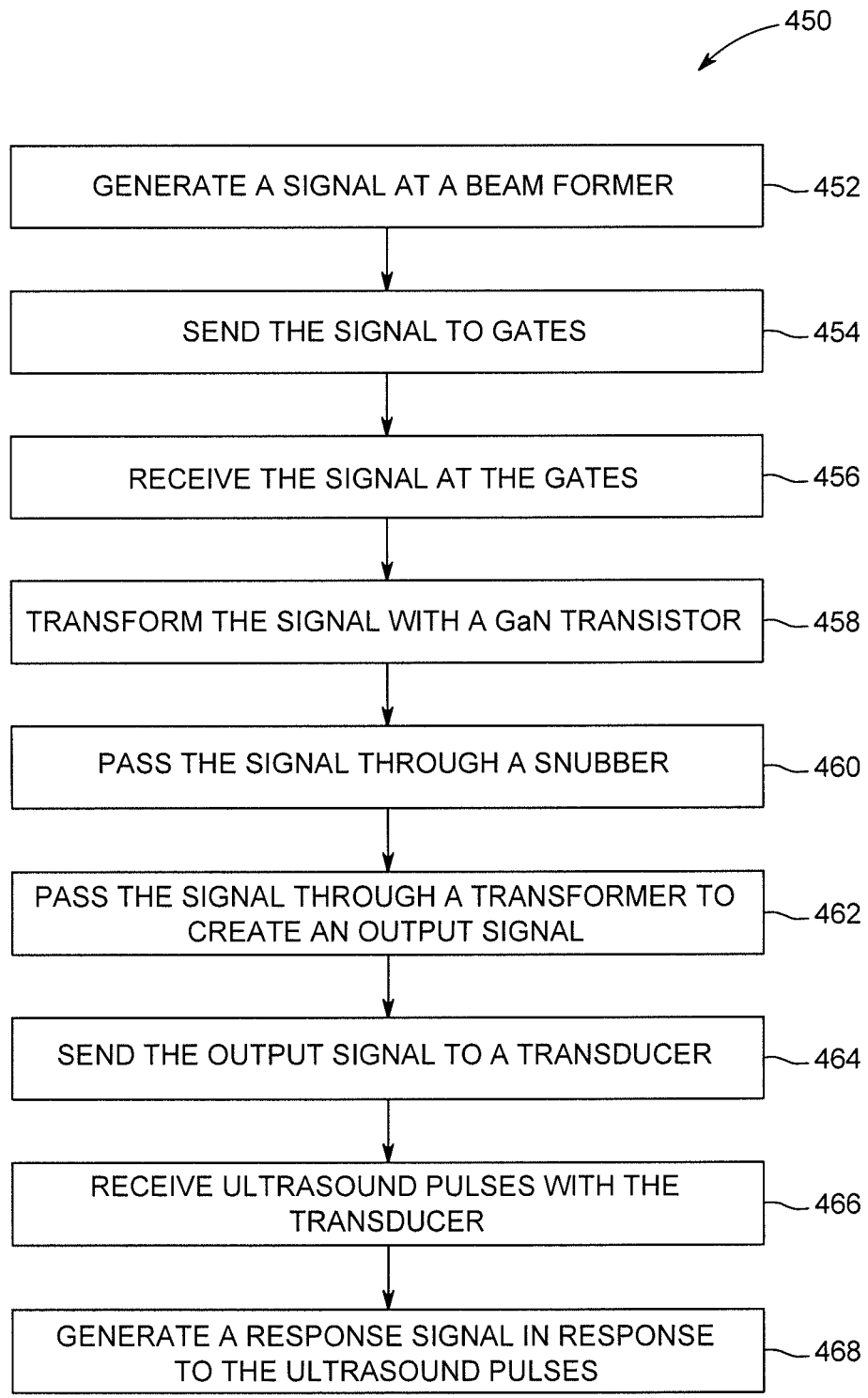
FIG. 8 is a flow chart depicting an embodiment of a method for generating a pulsed signal using a GaN pulse generator.

FIG. 8 is a flow chart illustrating an embodiment of a method 450 to generate a pulsed signal for use in the transducer array 14 using one or more of the circuits described herein. Although the following method 450 describes a number of operations that may be performed, it should be noted that the method 450 may be performed in a variety of suitable orders and/or all of the operations of the method 450 may not be performed.

The depicted method 450 includes generating (block 452) a signal at the transmitter beam former 122 and sending (block 454) the signal to the first gate driver 200 and the second gate driver 202. The signal is received (block 456) at the first gate driver 200 and the second gate driver 202 and subsequently transformed (block 458) into a first pulsed signal with the first GaN transistor (in the first gate driver leg) 204 and into a second pulsed signal with the second GaN transistor 206 (in the second gate drive leg). The first and second pulsed signals are passed (block 460) through the first snubber circuit 226 and second snubber circuit 228 respectively. The method 450 includes passing (block 462) the first pulsed signal and the second pulsed signal through the transformer 230 where the first pulsed signal and the second pulsed signal are combined into a single output signal. The output signal can then be sent (block 464) to the transducer array 14 where it is used to drive the array and to generate ultrasound pulses in response to the output signal. In the depicted example, the method 450 also includes receiving (block 466) backscattered ultrasound pulses using the transducer array 14 and generating (block 468) a response signal in response to the backscattered ultrasound pulses.

Figure 9:
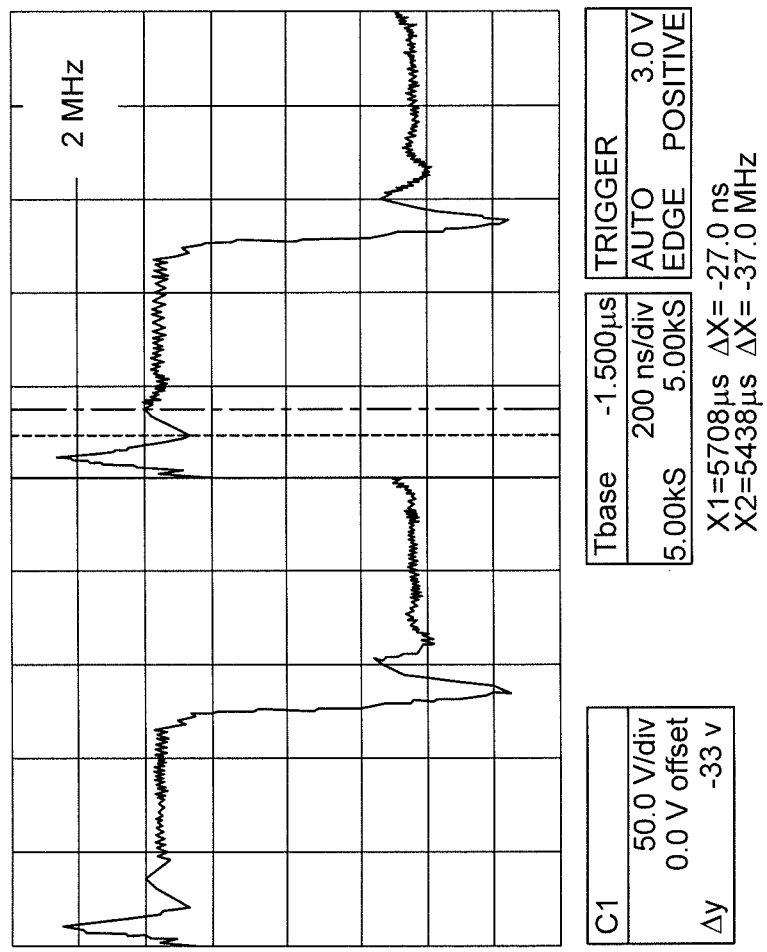
FIG. 9 is a graph of the performance of an embodiment of a GaN pulse generator operated at 2 MHz, in accordance with aspects of the present disclosure.
Figure 10:
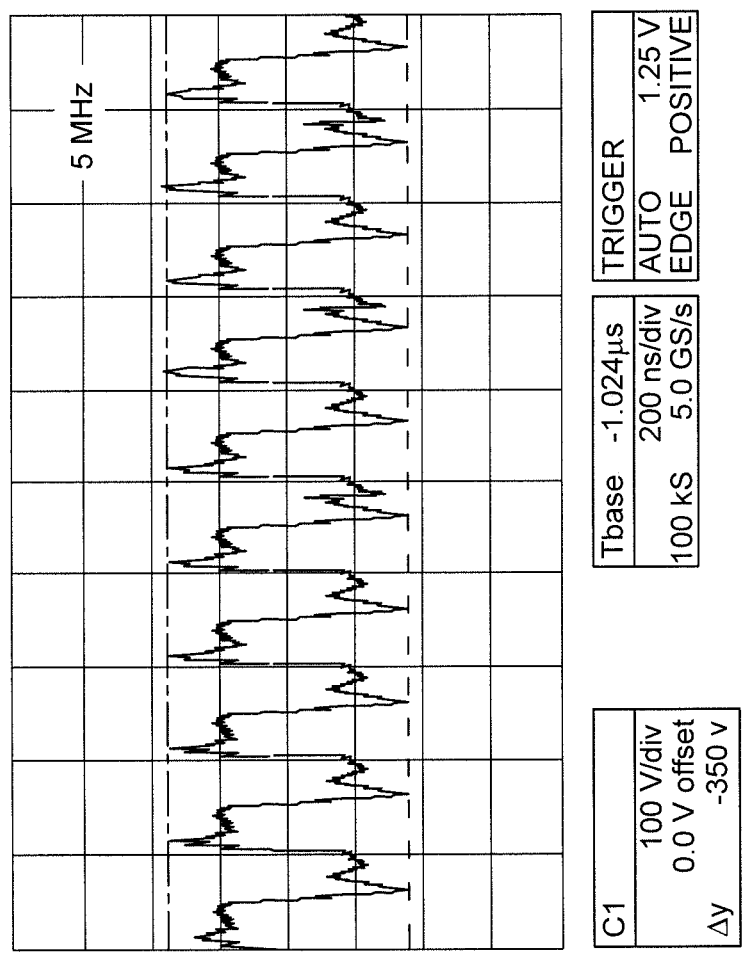
FIG. 10 is a graph of the performance of an embodiment of a GaN pulse generator operated at 5 MHz, in accordance with aspects of the present disclosure.
Figure 11:
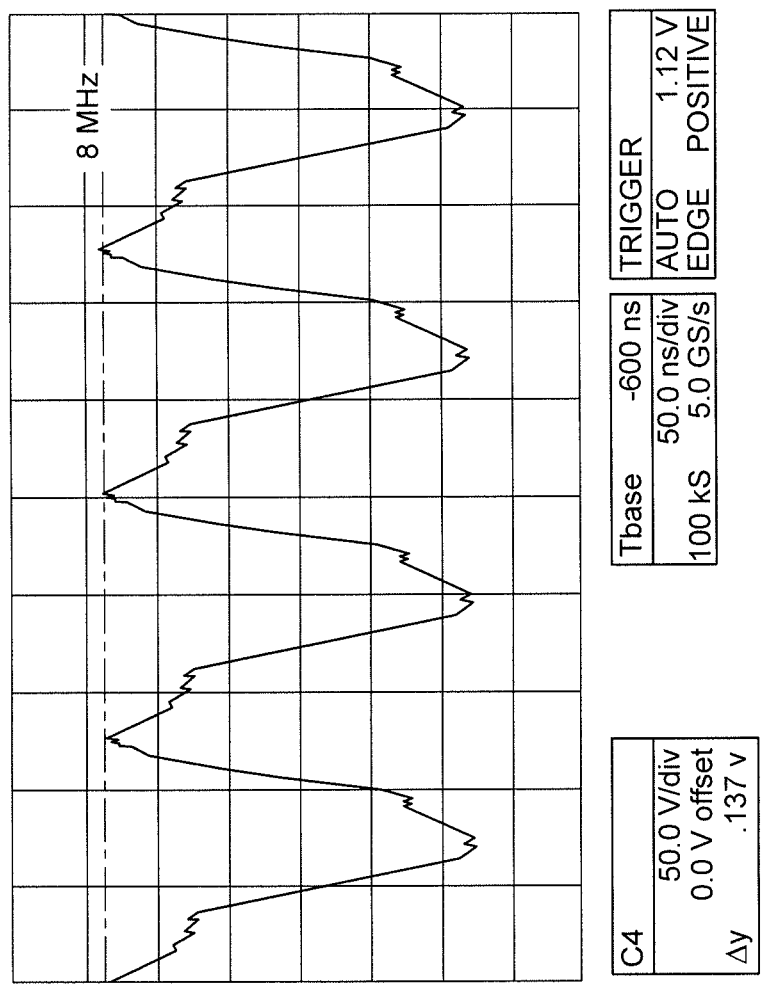
FIG. 11 is a graph of the performance of an embodiment of a GaN pulse generator operated at 8 MHz, in accordance with aspects of the present disclosure.
Figure 12:
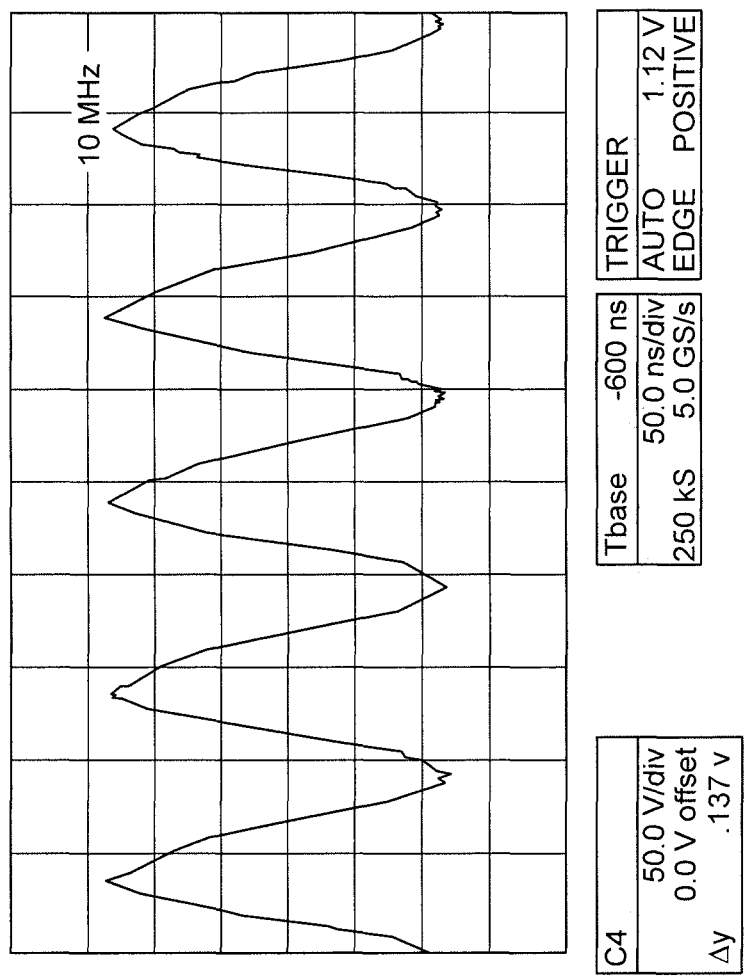
FIG. 12 is a graph of the performance of an embodiment of a GaN pulse generator operated at 10 MHz, in accordance with aspects of the present disclosure.

FIGS. 9 through 12 include waveform graphs of the response of an embodiment of the GaN pulse generator of FIG. 3 at different frequencies, however each output is generated with a resistor load of 100Ω. FIG. 9 depicts the response when the system is operating at 2 MHz. FIG. 10 depicts the response when the system is operating at 5 MHz. FIG. 11 depicts the response when the system is operating at 8 MHz. FIG. 12 depicts the response when the system is operating at 10 MHz.

Table 1 shows the results for a representative device for both a GaN-component based pulse generator, as shown in FIG. 3 and a comparable silicon-based component. In this example, the GaN component is an EPC2025 enhancement mode power transistor available from Efficient Power Conversion. The comparison silicon component is an Infineon IPD50R3K0CE high voltage power MOSFET with better output charges.

TABLE 1

| | VDS (V) | ID (A) | Rds_on (Ω) | Qg (nC) | Ciss (pF) | Coss (pF) | Size (mm²) | Thermal Impedance (° C./W) |
|---|---|---|---|---|---|---|---|---|
| GaN | 300 | 4 | 0.15 | 1.85 | 194 | 43 | 3.80 | 64 |
| Silicon | 550 | 1.7 | 3 | 4.3 | 78 | 5.5 | 39 | 50 |

As can be seen in Table 1, where parameters for the two comparison components are set forth, there are a number of benefits to using a GaN device over a silicon device in the ultrasound pulser context. For example, the GaN device is able to handle a higher power level than the silicon device, i.e., greater than 1.7 A, such as 4 A or greater. Further, the GaN device suffers twenty times less conduction loss at the same current, i.e., 0.15Ω compared to 3Ω. In addition, the GaN device can handle faster switching, i.e., 1.85 nC compared to 4.3 nC. Moreover, the GaN device delivers these benefits in a much smaller size, 3.80 mm² compared to 39 mm². Finally, the GaN device is able to withstand burst mode operation for as long as 50 milliseconds.

Figure 13:
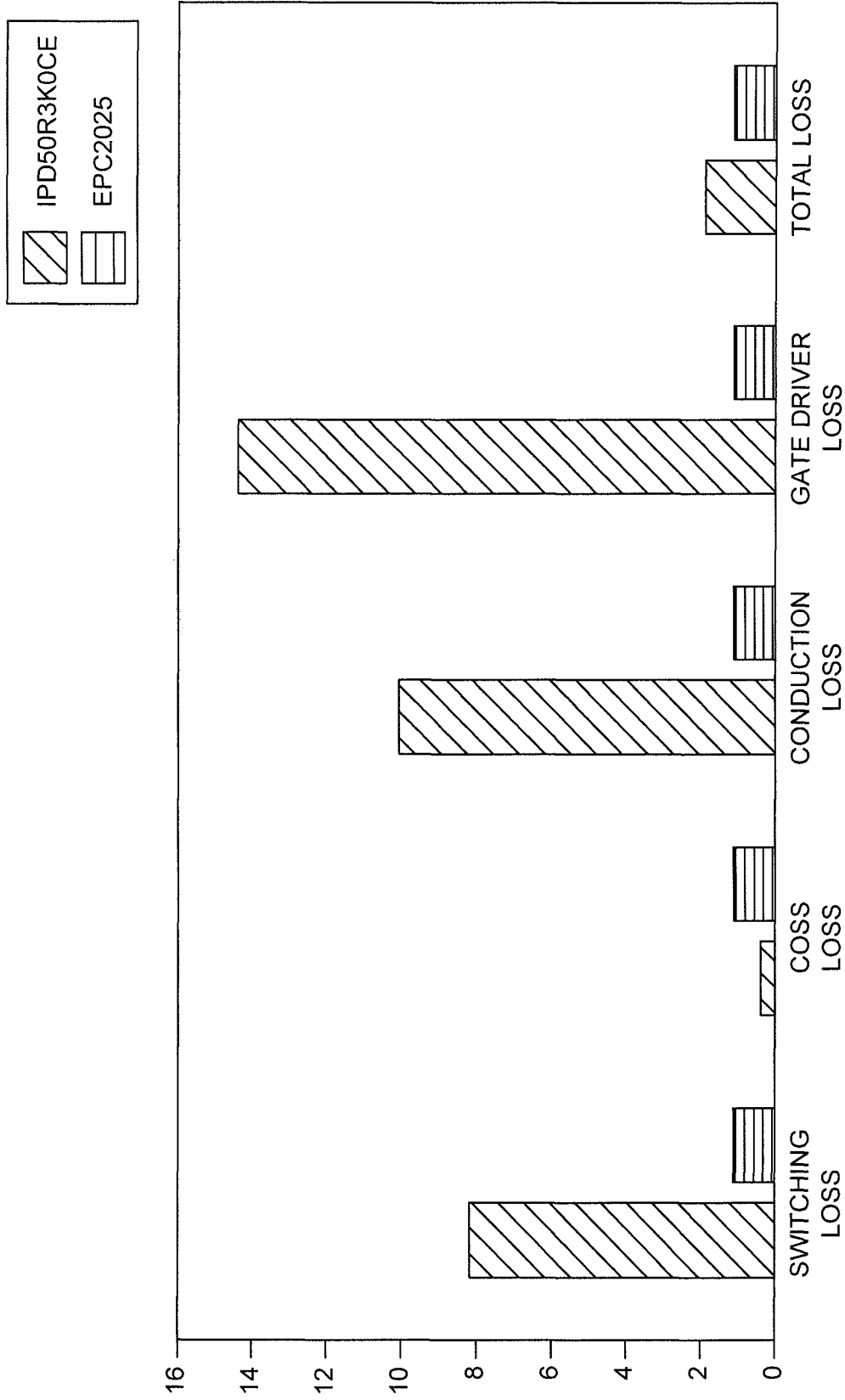
FIG. 13 is a graph of a comparison of various losses between a representative GaN device and a representative silicon device.

With the preceding in mind, FIG. 13 illustrates that the representative GaN device is able to achieve much lower losses compared to the representative silicon device. The losses are measured with a 90 V pulse amplitude, a 10 MHz pulse frequency, and a 100Ω load. The representative GaN device has much lower conduction and switching losses compared to the representative silicon device. The switching loss of the representative silicon device is eight times higher than the representative GaN device. The conduction loss of the representative silicon device is ten times higher than the representative GaN device. The gate driver loss of the representative silicon device is fourteen times higher than the representative GaN device. Although the representative GaN device has a higher Coss discharge loss than the representative silicon device, the total loss for the representative silicon device remains about 1.7 times higher than the total loss of the representative GaN device.

Figure 14:
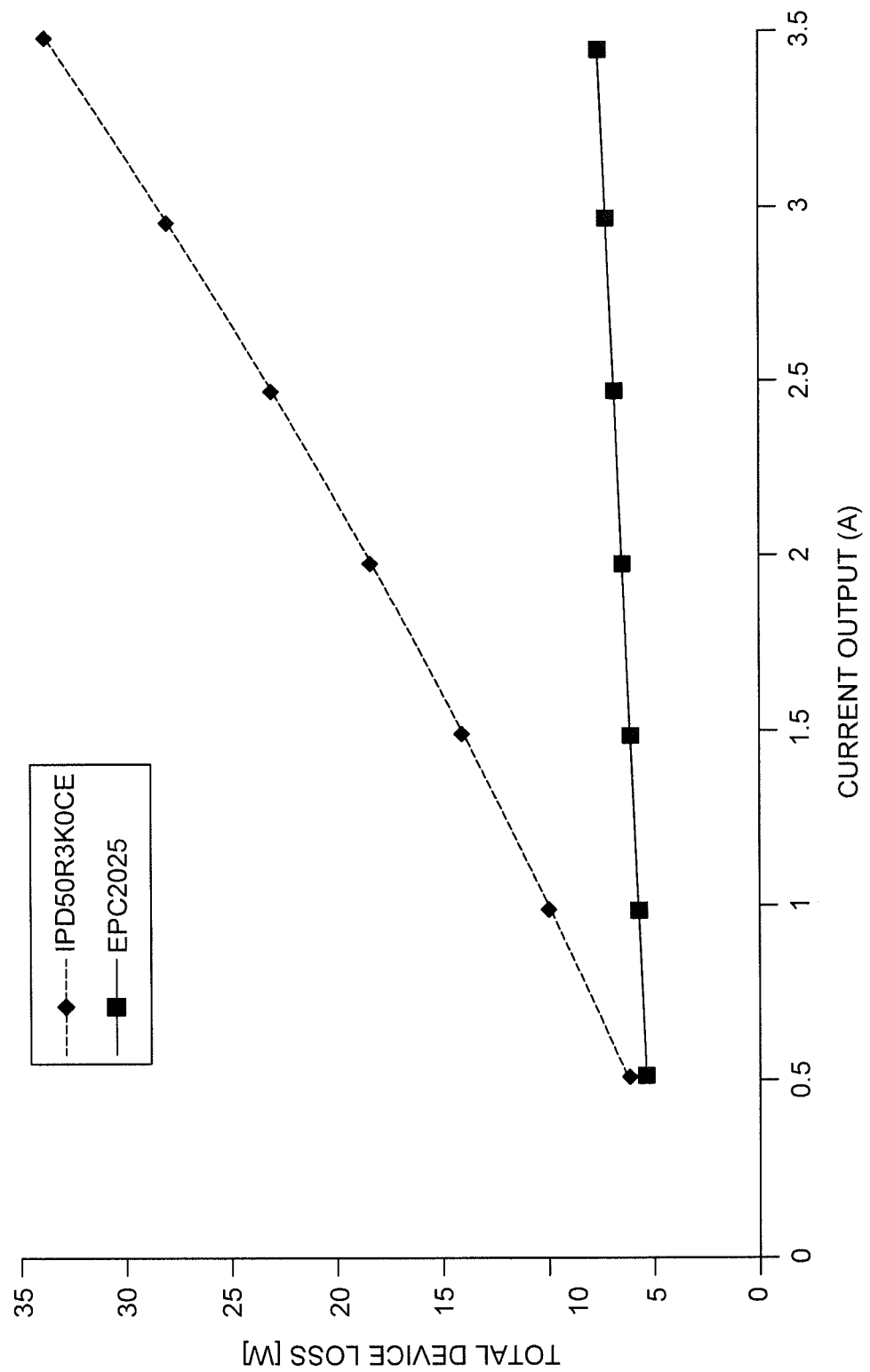
FIG. 14 is a graph of a comparison of the output current versus the total device loss between the representative GaN device and the representative silicon device.

FIG. 14 depicts the total device loss compared to the output current. The losses are measured with a 90 V pulse amplitude, a 10 MHz pulse frequency, and varying load currents. FIG. 14 elucidates that, as the output current increases, the total device loss of the silicon device compared to the GaN device increases greatly. For example, at an output current of 2 A, the total device loss of the representative silicon device is three times higher than the total device loss of the representative GaN device. In addition, at an output current of 3.5 A, the total device loss of the representative silicon device is 4.5 times higher than the total device loss of the representative GaN device.

Figure 15:
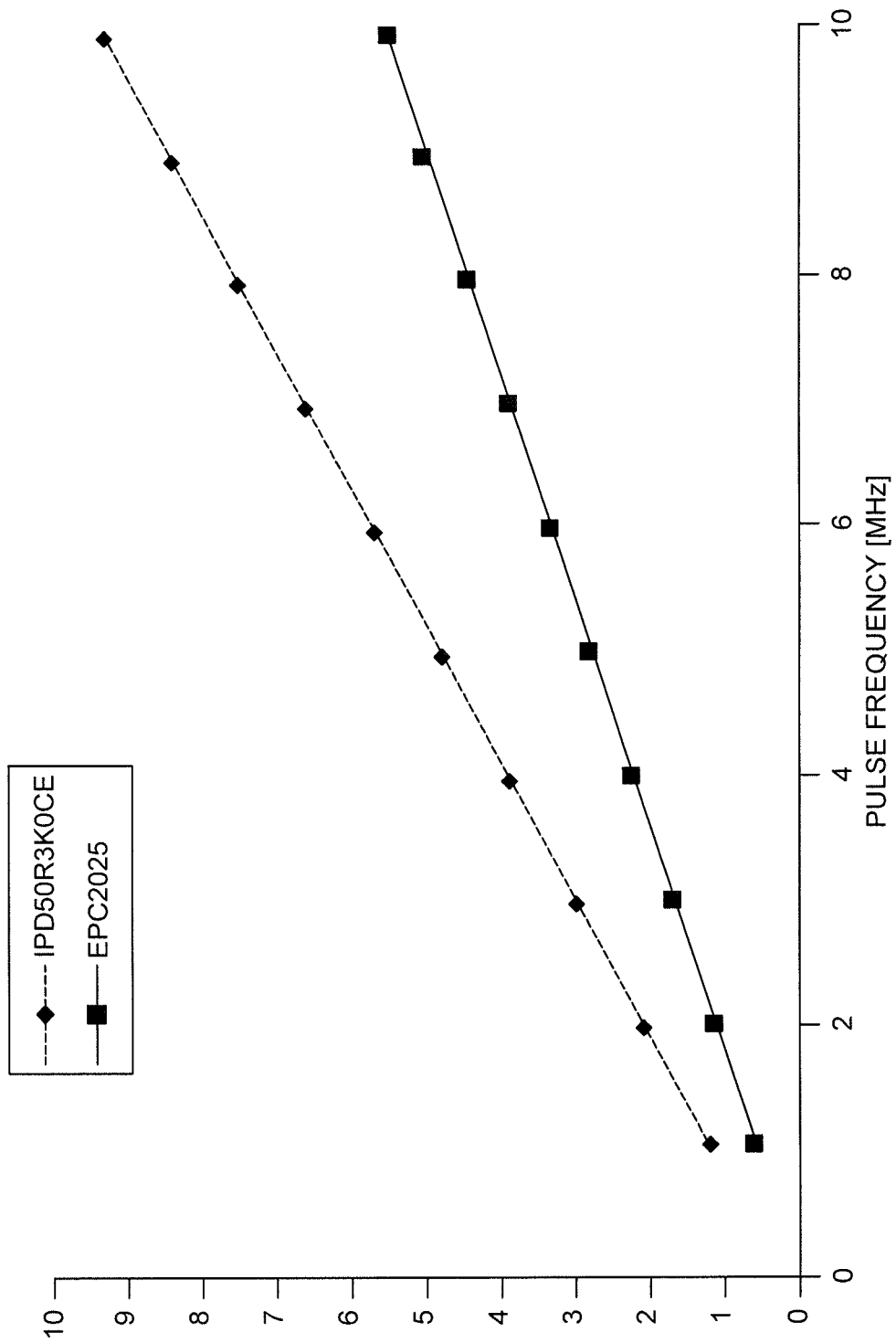
FIG. 15 is a graph of a comparison of the pulse frequency versus the total device loss between the representative GaN device and the representative silicon device.

FIG. 15 illustrates the total device loss compared to the pulse frequency for a silicon device and a GaN device. The losses are measured with a 90 V pulse amplitude, a 100Ω load, and varying pulse frequencies. As shown in FIG. 15, the total device loss remains lower at every frequency for the GaN device compared to the silicon device.

As discussed herein, it may be beneficial to utilize high power, high frequency pulsing in certain ultrasound applications. Utilizing GaN devices may achieve more desirable results over commonly used silicon devices in such contexts. GaN devices may lead to lower total device losses at a wide range of frequencies and may handle higher power levels. The benefits of the GaN device may also be conferred in a smaller form factor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound system comprising:
a transmitter beam former configured to send a signal;
a first gate driver electrically coupled to a first gallium nitride (GaN) transistor and the first gate driver is configured to receive the signal from the transmitter beam former;
a second gate driver electrically coupled to a second GaN transistor and the second gate driver is configured to receive the signal from the transmitter beam former;
a first snubber circuit and second snubber circuit, each comprising a respective capacitor and resistor, wherein each snubber circuit is configured to clamp a voltage overshoot when present;
a transformer configured to generate an output signal when operated, wherein the transformer is electrically connected downstream of the first GaN transistor, the second GaN transistor, the first snubber circuit, and the second snubber circuit, and wherein the transformer comprises a plurality of windings in a center tapped configuration;
a transmit/receive switch configured to receive the output signal; and a transducer array electrically coupled to the transmit/receive switch, wherein the transducer array generates ultrasound pulses in response to the output signal.

2. The ultrasound system of claim 1, comprising a power supply electrically coupled to the first snubber circuit, the second snubber circuit, and the transformer.

3. The ultrasound system of claim 1, wherein the first GaN transistor is electrically coupled to a first signal ground, the second GaN transistor is electrically coupled to a second signal ground, and the transformer is electrically coupled to a third signal ground.

4. The ultrasound system of claim 1, wherein the first snubber circuit is coupled to a fourth ground and the second snubber circuit is coupled to a fifth ground.

5. The ultrasound system of claim 1, wherein each of the first snubber circuit and the second snubber circuit comprises a respective diode.

6. The ultrasound system of claim 1, wherein the first GaN transistor and the second GaN transistor are configured to operate at approximately 1 megahertz or greater.

7. The ultrasound system of claim 1, wherein the first GaN transistor and the second GaN transistor are configured to withstand at least 1.7 amps in burst mode operation.

8. The ultrasound system of claim 1, wherein the first GaN transistor and the second GaN transistor are configured to withstand at least 4 amps in burst mode operation.

9. The ultrasound system of claim 1, wherein the first GaN transistor and the second GaN transistor are configured to sustain a burst mode for longer than 40 milliseconds.

10. The ultrasound system of claim 1, wherein the transducer array is configured to both generate and receive ultrasound waves, and wherein the transducer array generates a response signal in response to the received ultrasound waves.

11. The ultrasound system of claim 10, wherein the transmit/receive switch is electrically coupled to an analog-to-digital converter, and the analog-to-digital converter is configured to receive the response signal.

12. The ultrasound system of claim 11, wherein the analog-to-digital converter is electrically coupled to a receiver beam former, and the receiver beam former is configured to receive the response signal.

13. The ultrasound system of claim 12, wherein the receiver beam former is electrically coupled to a receiver, and the receiver is configured to receive the response signal, and the receiver generates a processed signal in response to the response signal.

14. The ultrasound system of claim 13, wherein the receiver is electrically coupled to a scan converter, and the scan converter is configured to receive the processed signal, and the scan converter converts the processed signal into an image.

15. A method of transforming a signal into a pulse for use in ultrasound, comprising:

receiving a signal at a first gate driver and a second gate driver;

transforming the signal from the first gate driver into a first pulsed signal with a first gallium nitride (GaN) transistor;

transforming the signal from the second gate driver into a second pulsed signal with a second GaN transistor;

passing the first pulsed signal through a first snubber circuit, wherein the first snubber circuit comprises a first resistor and a first capacitor;

passing the second pulsed signal through a second snubber circuit, wherein the second snubber circuit comprises a second resistor and a second capacitor; and passing the first pulsed signal and the second pulsed signal through a transformer, wherein the transformer comprises a plurality of windings in a center tapped configuration, and wherein the first pulsed signal and the second pulsed signal become a single output signal after passing through the transformer.

16. The method of claim 15, comprising sending the output signal to a transducer array that generates ultrasound pulses in response to the output signal.

17. The method of claim 16, comprising receiving backscattered ultrasound pulses with the transducer array and generating a response signal in response to the backscattered ultrasound pulses.

18. The method of claim 15, comprising generating the signal at a transmitter beam former and sending the signal to the first gate driver and the second gate driver.

19. The method of claim 15, wherein the first GaN transistor is electrically coupled to a first signal ground and the second GaN transistor is electrically coupled to a second signal ground.

20. An ultrasound pulse generator circuit comprising:

a first gate driver electrically coupled to a first gallium nitride (GaN) transistor and the first gate driver is configured to receive a signal from a transmitter beam former;

a second gate driver electrically coupled to a second GaN transistor and the second gate driver is configured to receive the signal from the transmitter beam former;

a first snubber circuit and second snubber circuit, each comprising a respective capacitor and resistor, wherein each snubber circuit is configured to clamp a voltage overshoot when present; and a transformer configured to generate an output signal suitable for driving an ultrasound transducer array, wherein the transformer is electrically connected downstream of the first GaN transistor, the second GaN transistor, the first snubber circuit, and the second snubber circuit, and wherein the transformer comprises a plurality of windings in a center tapped configuration.

* * * * *